United States Patent [19]

Rubin

[11] Patent Number: 5,670,142
[45] Date of Patent: Sep. 23, 1997

[54] TREATMENT FOR ITCH OF CHICKEN POX

[75] Inventor: Stan Michael Rubin, Troy, N.Y.

[73] Assignee: Donald Neudecker, Johnsonville, N.Y.; a part interest

[21] Appl. No.: 676,814

[22] Filed: Jul. 8, 1996

[51] Int. Cl.$^6$ ..................................................... A61K 7/48
[52] U.S. Cl. .................. 414/78.05; 424/450; 424/94.21; 424/96.45; 424/405; 514/886; 514/887; 514/862; 514/873
[58] Field of Search ........................... 514/886, 887, 514/862, 873, 969, 772.4; 424/78.05, 94.21, 94.1, 96.45, 405, 450

[56] References Cited

U.S. PATENT DOCUMENTS

| | | | |
|---|---|---|---|
| 4,166,108 | 8/1979 | Brown | 424/28 |
| 4,331,653 | 5/1982 | Brown | 424/28 |
| 5,441,740 | 8/1995 | Ozien | 424/401 |
| 5,444,096 | 8/1995 | MccreA | 514/770 |
| 5,476,853 | 12/1995 | Cauwenbergh | 514/253 |
| 5,543,149 | 8/1996 | Rubin | 424/405 |

FOREIGN PATENT DOCUMENTS 0 102 410  2/1984  European Pat. Off. .

OTHER PUBLICATIONS

Hagermark, Osten; Influence of Antihistamines, Sedatives, and Aspirin on Experimental Itch; Acta Derm. Venerol. (1973), 53(5) pp 363–368 Dec. 3, 1973.

Davies et al.; The efficacy of Histamine Antagonists as Antipruritics in Experimentally Induce Pruritis; Archives of Dermatogolog Research (1979), 266(2), 117–20 Dec. 1, 1979.

*Primary Examiner*—Thurman K. Page
*Assistant Examiner*—Diedra Faulkner
*Attorney, Agent, or Firm*—Heslin & Rothenberg, P.C.

[57] ABSTRACT

A method for reducing the itch and the scarring associated with chicken pox is disclosed. The method entails applying a topical pharmaceutical formulation of papain, pancreatin or subtilisin to the skin proximate to the vesicles. To further reduce scarring, an antibiotic is applied with the papain, pancreatin or subtilisin. Compositions are provided in the form of solutions, lotions, ointments and salves containing papain, pancreatin or subtilisin and, optionally, a surfactant, an antibiotic and a penetration enhancer.

21 Claims, No Drawings

TREATMENT FOR ITCH OF CHICKEN POX

FIELD OF THE INVENTION

The invention relates to a method for reducing the itch associated with chicken pox (varicella). The method entails applying a topical pharmaceutical formulation of papain, pancreatin or subtilisin to the skin proximate to the varicella vesicles.

BACKGROUND OF THE INVENTION

Varicella (chicken pox) is a common contagious disease, most often of childhood, that is caused by primary infection with varicella-zoster virus (VZV). It is characterized by a short or absent prodromal period and by a pruritic rash consisting of crops of papules, vesicles, pustules, and eventual crusting of nearly all the lesions. In normal children the systemic symptoms are usually mild, and serious complications are unusual.

VZV, a member of the herpesvirus group is composed of an inner core containing protein and DNA, an icosahedral capsid surrounded by a tegument, and an outer lipid-containing envelope. Glycoproteins specified by VZV are present both on the membranes of infected cells and on the envelope of the virus itself.

Chicken pox is highly infectious. It is not absolutely certain how the virus is transmitted. Vesicle fluid is infectious and it is possible that the virus may be transmitted by contact between children in some instances. Non-immune individuals may contact chicken pox from zoster patients. It is possible that in the early stages of chicken pox when lesions are present in the throat, droplets containing virus are spread by the patient and inhaled by others. The virus is also spread, presumably through contact with vesicle fluid, to others, or vesicle material is dispersed on dust particles and inhaled.

The incubation period of chicken pox is about two weeks, although as little as seven days and as much as 23 days have been reported. In children the characteristic feature of chicken pox is the absence of prodromal symptoms; the first manifestation of the illness is an itchy rash. In very small children it may be transient. In older children the rash is more obvious and more itchy, and still more severe in adults. The typical vesicle of chicken pox is superficially located in the skin. It has thin fragile walls that rupture easily. In appearance it resembles a dewdrop, usually elliptical in shape, 2 to 3 mm in diameter, and surrounded by an erythematous material. This red areola is most distinct when the vesicle is fully formed and becomes pustular, and it fades as the lesion begins to dry. The drying process, which begins in the center of the vesicle or pustule, produces an umbilicated appearance and eventually a crust. After a variable interval of 5 to 20 days, depending on the depth of skin involvement, the scab falls off, leaving a shallow pink depression. The site of the lesion becomes white, with no evidence of scar formation.

Secondarily infected lesions are by far the commonest complication. Prematurely removed scabs (due to scratching by the patient) and scratching the itchy vesicles cause environmental bacteria, usually *Staphylococcus aureus*, to be introduced into lesions. This will in most cases be followed by permanent scarring, particularly on the face, where the lesions are denser than other parts of the body. Thus, a pharmaceutical composition that both reduced the itch and inhibited secondary infection would act synergistically to minimize scarring.

For decades, and through to the present, calamine lotion or some other symptomatic remedy has been used; however, no remedy has ever proved effective against the itch, scratching of which leads to the aforementioned secondary infection and permanent scarring.

SUMMARY OF THE INVENTION

The present invention is directed to a method and compositions for reducing the itching associated with chicken pox. The method comprises applying a therapeutically effective amount of papain, pancreatin, subtilisin or a combination thereof in a suitable pharmaceutical carrier to the surface of the skin proximate to the varicella vesicles. The pharmaceutical carrier may be water based or primarily lipid and preferably contains, in addition, one or more of an antibiotic, a surfactant, and a penetration enhancer. The incorporation of an antibiotic provides a method to minimize the scarring that arises from secondary infection.

A closely related aspect of the invention is, therefore, a method for reducing scarring resulting from chicken pox comprising applying a combination of an effective amount of an itch-reducing pharmaceutical composition and an effective amount of an antibiotic to the surface of a patient's skin proximate to a pox vesicle. As before the itch-reducing composition contains an enzyme chosen from the group consisting of papain, pancreatin and subtilisin in a pharmaceutical carrier In another aspect the invention relates to pharmaceutical compositions for treating chicken pox comprising in combination: (a) an itch-reducing amount of an enzyme chosen from the group consisting of papain, pancreatin and subtilisin; (b) an antibiotic; (c) a surfactant; and (d) a pharmaceutical carrier adapted for topical application. The carrier may be a solution, a lotion, an ointment or a salve. Preferred antibiotics include neomycin, bacitracin, polymixin and mixtures thereof. Preferred surfactants include ammonium lauryl sulfate, lauramide DEA, cocamidopropyl betaine and mixtures thereof.

The composition may additionally comprise a penetration enhancer, which may be N-methyl-2-pyrrolidone, oleic acid, linoleic acid, isopropyl linoleate or a terpene. The terpene may be menthol, carvone, carveol, dihydrocarveol, dihydrocarvone, neomenthol, isopulegol, terpene-4-ol, menthone, pulegol, camphor, geraniol, α-terpineol, citral, linalol, carvacrol, thymol, anethole or a mixture thereof.

The pharmaceutical composition may additionally comprise urea, lecithin or mixtures thereof, which function both as penetration enhancers and surfactants.

DETAILED DESCRIPTION OF THE INVENTION

The method comprises applying a therapeutically effective amount of papain, pancreatin, subtilisin or a combination thereof in a suitable pharmaceutical carrier to the surface of the skin. The active ingredients in the methods and compositions of the invention are papain (Chemical Abstracts Registry No. 9001-73-4), subtilisin (Chemical Abstracts Registry No. 9014-01-1) and pancreatin (Chemical Abstracts Registry No. 8049-47-6); all are commercially available.

The compositions comprise four principal ingredients: (a) an enzyme chosen from the group consisting of papain, pancreatin and subtilisin; (b) an antibiotic; (c) a surfactant; and (d) a pharmaceutical carrier adapted for topical application.

The antibiotic may be chosen from any of those that are topically active against pathogenic bacteria found on the surface of the skin. The purpose of the antibiotic is to prevent secondary infection of the vesicle, primarily by opportunistic Staphylococcus species. Neomycin, bacitracin, polymyxin are inexpensive, safe and effective, but others (e.g. zinc pyrithione, chloramphenicol, nitrofurazone, metronidazole, silver sulfadiazine) may be used as well.

The surfactant may be anionic, cationic, amphoteric or nonionic, and all are well-known to persons in the art. Whatever the surfactant, it is important to maintain a final pH of the composition in the range of 4 to 9, and 6 to 7 is preferred. The surfactant will, if present, generally comprise from 1 to 25% by weight of the composition.

The topical pharmaceutical carrier may include any substance capable of dispersing and maintaining contact between the active ingredients and the skin. The vehicle may be glycerin, alcohol or water based. Examples of such vehicles include aloe vera which is a gel base, together with ethanol, isopropyl alcohol, water, propylene glycol and a non-ionic surfactant such as laureth-4. Other water-based alcohol/glycerin vehicles and carriers are within the scope of the present invention. A typical water-based lotion will contain from 45 to 50 parts of glycerin, one to three parts Tween 80™, from 45 to 50 parts of water and from 1 to 50 papain, pancreatin or subtilisin.

Also included in the scope of the invention are ointments, emulsions or dispersions in which water, if present, is a minor constituent. Typical ointment formulation comprises from 90 to 98 parts of a mixture of petrolatum, mineral oil, mineral wax and wool wax alcohol, from 0.5 to 3 parts of a mixture of polyoxyethylene and sorbitan monooleate (Tween 80™), from 1 to 5 parts of water, and from 1 to 50 parts papain, pancreatin or subtilisin. Another suitable non-aqueous ointment can be prepared from 95 parts of liquid petrolatum usp, 5 parts polyethylene and from 1 to 50 parts of the appropriate enzyme. The resulting ointment spreads easily and has an even consistency over wide temperature extremes. It is, in addition, non-irritating and non-sensitizing.

Formulations of the enzymes of interest may also be prepared containing from 0 to 25% by weight of urea. In general, in such urea containing ointments, the water content will vary from 5 to 50% by weight of the composition. Any suitable ointment carrier may be used such as lanolin, ethylene glycol polymers and the like. In the case of formulations containing urea, it is known in the art that borate salts may often be added to stabilize the pharmaceutical composition (see U.S. Pat. No. 2,917,433).

Other materials, which may act as penetration enhancers may be added as described above for urea. Typical terpene penetration enhancers include menthol, carvone, carveol, dihydrocarveol, dihydrocarvone, neomenthol, isopulegol, terpene-4-ol, menthone, pulegol, camphor, geraniol, α-terpineol, citral, linalol, carvacrol, thymol and anethole. Menthol and camphor are preferred. The composition must, however, be free of salicylates.

Water based compositions may also be employed, in which case the enzyme will commonly be in solution and the aqueous solution may, if desired, be thickened with a suitable gel to provide a less mobile composition. Such compositions are well known in the art. In the water based compositions, the enzyme will once again be present in an amount from 1 to 50% by weight.

A topical ointment may be prepared employing purified enzymes from ICN Biomedicals, Inc. (Irvine, Calif.) by dispersing pancreatin alone or all three enzymes together (about 125 µg of pancreatin; about 10 µg of papain and 10 µg of subtilisin) in about 10 mL of hydrophilic ointment base (available as NDC 0168-0047-16 from Fougera, Inc., Mellville, N.Y.) to which has been added about 250 mg of urea dissolved in about 2–3 mL of water; 30 mg of ammonium lauryl sulfate, lauramide DEA or cocamidopropyl betaine and 5000 units per gram of ointment of polymyxin B sulfate. The polymyxin B sulfate may be replaced with or supplemented with 400 units per gram of bacitracin or 3.5 to 4 mg of neomycin sulfate. Menthol (5 mg) and camphor (5 mg) may be added. The pH of the final ointment should be between 4 and 8.

While the invention has been particularly shown and described with reference to preferred embodiments thereof, it will be understood by those skilled in the art that other changes in form and details may be made therein without departing from the spirit and scope of the invention. In particular, it will be obvious to those of skill in the art that combinations of the foregoing enzymes will function in a similar manner to the individual enzymes.

I claim:

1. A method for reducing the itch associated with chicken pox comprising applying an effective amount of an itch-reducing pharmaceutical composition to the surface of a patient's skin proximate to a pox vesicle, said itch-reducing composition containing an enzyme chosen from the group consisting of papain, pancreatin and subtilisin in a pharmaceutical carrier.

2. A method according to claim 1 wherein said enzyme is papain.

3. A method according to claim 1 wherein said enzyme is pancreatin.

4. A method according to claim 1 wherein said enzyme is subtilisin.

5. A method according to claim 1 wherein said itch-reducing composition additionally contains an antibiotic.

6. A method according to claim 1 wherein said itch-reducing composition additionally contains a surfactant.

7. A method according to claim 1 wherein said itch-reducing composition additionally contains a penetration enhancer.

8. A method for reducing scarring resulting from chicken pox comprising applying a combination of an effective amount of an itch-reducing pharmaceutical composition and an effective amount of an antibiotic to the surface of a patient's skin proximate to a pox vesicle, said itch-reducing composition containing an enzyme chosen from the group consisting of papain, pancreatin and subtilisin in a pharmaceutical carrier.

9. A method according to claim 8 wherein said itch-reducing composition additionally contains a surfactant.

10. A method according to claim 8 wherein said itch-reducing composition additionally contains a penetration enhancer.

11. A method according to claim 1 or claim 7 wherein said enzyme is applied as a solution in an aqueous pharmaceutical carrier.

12. A method according to claim 1 or claim 7 wherein said enzyme is applied as an emulsion or dispersion in a lipid-containing pharmaceutical carrier.

13. A pharmaceutical composition for treating chicken pox comprising in combination:
   a. an itch-reducing amount of an enzyme chosen from the group consisting of papain, pancreatin and subtilisin;
   b. an antibiotic;
   c. a surfactant; and d. a pharmaceutical carrier adapted for topical application.

14. A pharmaceutical composition according to claim 13 wherein said antibiotic is chosen from the group consisting of neomycin, bacitracin, polymixin and mixtures thereof.

15. A pharmaceutical composition according to claim 13 wherein said surfactant is chosen from the group consisting of ammonium lauryl sulfate, lauramide DEA, cocamidopropyl betaine and mixtures thereof.

16. A pharmaceutical composition according to claim 13 additionally comprising a penetration enhancer.

17. A pharmaceutical composition according to claim 16 wherein said penetration enhancer is chosen from the group consisting of: N-methyl-2-pyrrolidone; oleic acid; linoleic acid; isopropyl linoleate; and a teterpene.

18. A pharmaceutical composition according to claim 17 wherein said terpene is chosen from the group consisting of menthol, camphor, and thymol.

19. A pharmaceutical composition according to claim 13 additionally comprising urea or lecithin.

20. A pharmaceutical composition in the form of an ointment or salve, according to any of claims 13 to 19.

21. A pharmaceutical composition in the form of a lotion or solution, according to any of claims 13 to 19.

* * * * *